United States Patent [19]

Hall et al.

[11] Patent Number: 5,162,352

[45] Date of Patent: Nov. 10, 1992

[54] 7-OXABICYCLOHEPTYL SUBSTITUTED HETEROCYCLIC AMIDE PROSTAGLANDIN ANALOGS

[75] Inventors: Steven E. Hall, Pennington, N.J.; Martin L. Ogletree, Newtown, Pa.

[73] Assignee: E. R. Squibb & Sons, Inc., Princeton, N.J.

[21] Appl. No.: 748,379

[22] Filed: Aug. 22, 1991

[51] Int. Cl.$^5$ .................. A61K 31/42; C07D 498/02
[52] U.S. Cl. ................... 514/374; 548/236; 548/303.7; 548/304.1
[58] Field of Search .......... 548/236; 514/374

[56] References Cited

U.S. PATENT DOCUMENTS 4,977,174 12/1990 Stein et al. ............ 514/397
5,100,889 3/1992 Misra et al. ............ 514/374

FOREIGN PATENT DOCUMENTS 374952 6/1990 European Pat. Off. .
391652 10/1990 European Pat. Off. .

Primary Examiner—Donald G. Daus
Attorney, Agent, or Firm—Burton Rodney

[57] ABSTRACT

7-Oxabicycloheptyl substituted heterocyclic amide prostaglandin analogs are provided which are thromboxane $A_2$ ($TXA_2$) receptor antagonists and have the structural formula

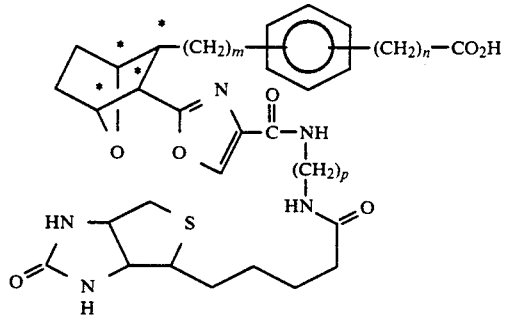

wherein m is 1, 2 or 3, n is 1, 2, 3 or 4 and p is 2 to 18.

These compounds are also useful in identifying thromboxane receptors in various tissue.

12 Claims, No Drawings

7-OXABICYCLOHEPTYL SUBSTITUTED HETEROCYCLIC AMIDE PROSTAGLANDIN ANALOGS

DESCRIPTION OF THE INVENTION

The present invention relates to 7-oxabicycloheptyl substituted heterocyclic amide prostaglandin analogs which are thromboxane $A_2$ ($TXA_2$) receptor antagonists or combined thromboxane $A_2$ receptor antagonist/thromboxane synthetase inhibitor useful, for example, in the treatment of thrombotic and/or vasospastic disease, and may be used as a tool to identify $TXA_2$ receptors in tissues. These compounds have the structural formula I

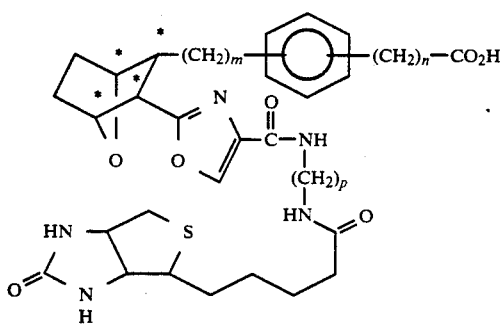

and including all stereoisomers thereof, wherein
m is 1, 2 or 3, preferably 1 or 2,;
n is 1, 2, 3 or 4 preferably 2 or 3; and
p is 2 to 18, preferably 4 to 12.
Preferred are compounds of formula Ix

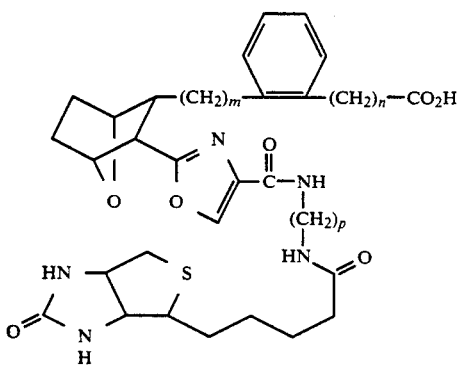

where m is 1, n is 2 or 3 and p is 4 to 12.

The compounds of formula I of the invention may be prepared as follows.

The activated ester of biotin having the structure A

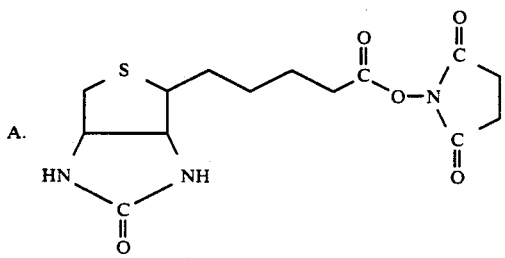

is made to undergo a condensation reaction with an α, ω-diamine II $$H_2N-(CH_2)_p-NH_2 \qquad II$$

in the presence of an aprotic polar solvent such as dimethylformamide (DMF) or dimethylsulfoxide (DMSO). The reaction mixture is stirred for about 2 to about 20 hours at a temperature within the range of from about 0° to about 40° C., preferably from about 0° to about 30° C., to form the amine III

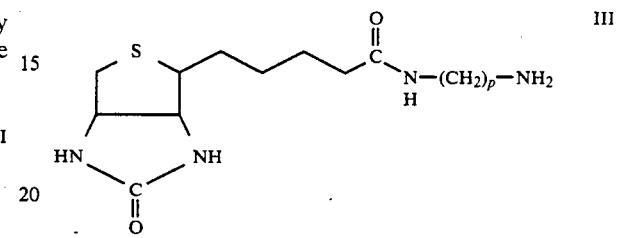

The above reaction is carried out employing a molar ratio of A:II of within the range of from about 0.5:1 to about 0.01:1, preferably from about 0.2:1 to about 0.05:1.

Amine III is reacted with acid chloride IV

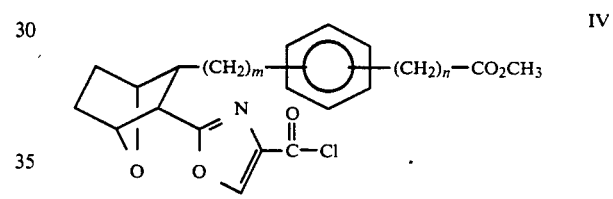

in a molar ratio of III:IV of within the range of from about 2:1 to about 0.5:1, and preferably from about 1.2:1 to about 0.8:1, at a temperature of within the range of from about 0° to about 25° C., preferably from about 10° to about 25° C., in the presence of an inert organic solvent such as methylene chloride or chloroform and an amine base such as triethylamine, tributylamine or pyridine, to form ester V

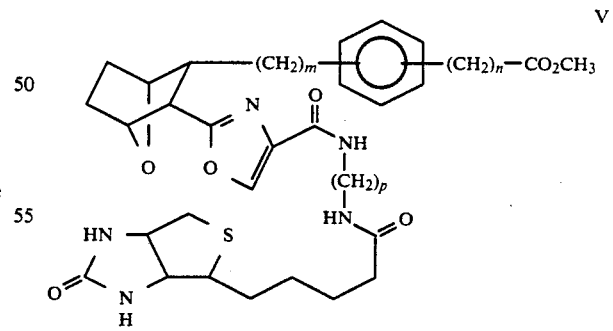

Ester V is then hydrolyzed by treatment with an alkali metal hydroxide such as lithium hydroxide or sodium hydroxide in the presence of a solvent or a mixture of solvents such as methanol, water or tetrahydrofuran, to form the acid I.

The starting acid chloride IV may be prepared as disclosed in European Patent Application No. 0391652 which corresponds to U.S. application Ser. No. 540,026 filed Jun. 18, 1990, now U.S. Pat. No. 5,100,889 which is incorporated herein by reference.

The compounds of this invention have four centers of asymmetry as indicated by the asterisks in formula I. However, it will be apparent that each of the formulae set out above which do not include asterisks still represent all of the possible stereoisomers thereof. All of the various stereo-isomeric forms are within the scope of the invention.

The various stereoisomeric forms of the compounds of the invention, namely, cis-exo, cisendo and all trans forms and stereoisomeric pairs may be prepared by employing starting materials and following the procedures as outlined in U.S. Pat. No. 4,143,054. Examples of such stereoisomers are set out below.

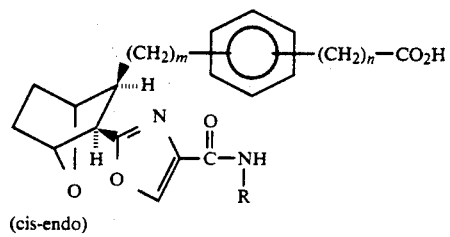
(cis-endo)

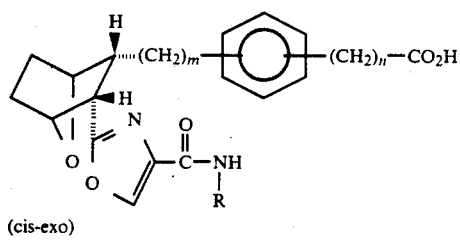
(cis-exo)

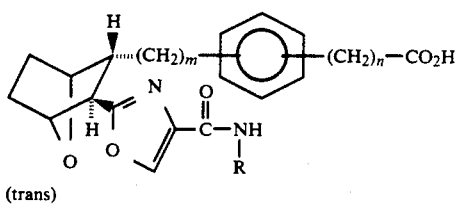
(trans)

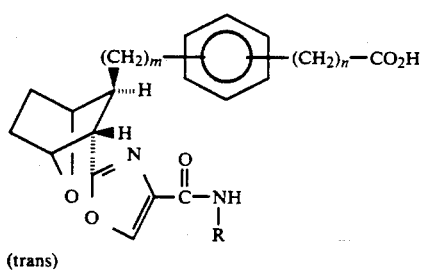
(trans)

where R in formulae Ia-Id is

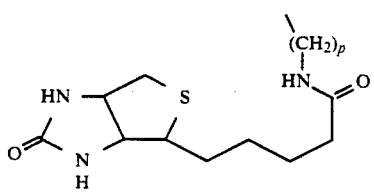

The nucleus in each of the compounds of the invention is depicted as

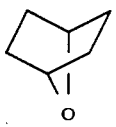

for matter of convenience; it will also be appreciated that the nucleus in the compounds of the invention may be depicted as

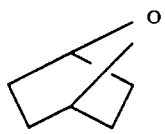

The compounds of this invention are thromboxane receptor antagonists and as such are useful as inhibitors of thromboxane receptor mediated actions. The term "thromboxane receptor antagonist" includes compounds which are so-called thromboxane $A_2$ receptor antagonists, thromboxane $A_2$ antagonists, thromboxane $A_2$/prostaglandin endoperoxide antagonists, TP-receptor antagonists, or thromboxane antagonists.

The compounds of the invention are also thromboxane synthetase inhibitors and thus are useful as inhibitors of thromboxane production.

The compounds of the invention are conjugates of a thromboxane $A_2$ receptor antagonist and biotin. As such, the compounds of the invention may be used as a tool to identify thromboxane $A_2$ receptors in various tissues.

In addition, compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication. They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including, platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, or hemolytic uremic syndrome, systemic lupus, cyclosporine-induced renal toxicity, pulmonary hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restore blood flow. For example, these compounds may be useful for improving postischemic myocardial function and decreasing myocardial infarct size. Ischemia caused by reduced blood flow during diagnostic or therapeutic procedures may benefit by treatment with these compounds, for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastases and tardive dyskinesia. The compounds may be useful in potentiating diuretic-induced diuresis.

In addition, the thromboxane receptor antagonists of the invention may be used with a thrombolytic agent such as t-PA, streptokinase, urokinase, prourokinase or anisoylated plasminogen-streptokinase activator complex (APSAC) within 6 hours of a myocardial infarction. In such case, the thrombolytic agent may be used in amounts conventionally employed, for example, as disclosed in the Physicians' Desk Reference for reducing post-ischemic myocardial injury.

The compounds of the invention can be administered orally or parenterally, preferably parenterally, to various mammalian species known to be subject to such maladies, e.g., humans, cats, dogs and the like in an effective amount within the dosage range of about 0.1 to about 100 mg/kg, preferably about 0.2 to about 50 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

Example 1

[1S-(1α,2α,3α,4α)]-2-[[3-[4-[[[8-[[5-(Hexahydro-2-oxo-1H-thieno[3,4-d]imidazol-4-yl)-1-oxopentyl]amino]octyl]amino]carbonyl]-2-oxazolyl-7-oxabicyclo[2.2.1]hept-2-yl]methyl]benzenepropanoic acid A. N-(8-Aminooctyl)biotinamide To a stirred mixutre of 4.4 g of 1,8-diaminooctane (30.6 mmol) in 30 mL of dimethylformamide (DMF) was added 0.707 g (2.07 mmol) of biotin-N-hydroxysuccinamide ester. The reaction mixture was stirred at 23° C. for 16 hours at which time $CH_3OH$ was added to obtain a homogeneous solution. The reaction mixture was stirred for an additional 4 hours and then was concentrated in vacuo. The residue was triturated with 100 mL of diethyl ether (ether), diluted with an additional 100 mL of ether and filtered to remove solids. The filter cake was stirred with 50 mL of ethyl acetate and this mixture was filtered. The remaining solid was slurried in approximately 40 mL of water. Some dissolution occurred, with the remaining solid turning into a gel. The water was removed by decantation and the gel was dissolved in 5:1 $CHCl_3/CH_3OH$. The resulting solution was filtered to remove particulates, dried quickly over $MgSO_4$, filtered and concentrated in vacuo to afford 380 mg (50%) of crude title amine which was used without further purification.

B. [1S-(1α,2α,3α,4α)]-2-[[3-[4-[[[8-[[5-(Hexahydro-2-oxo-1H-thieno[3,4-d]imidazol-4-yl)-1-oxyopentyl]amino]octyl]amino]carbonyl]-2-oxazolyl]-7-oxabicyclo[2.2.1]hept-2-yl]-methyl]benzenepropanoic acid, methyl ester To a stirred solution of 550 mg of [1S-(1α, 2α,3α,4α)]-2-[[3-(4-carboxy-2-oxazolyl)-7-oxabicyclo[2.2.1]hept-2-yl]methyl]benzenepropanoic acid, (prepared as described in U.S. application Ser. No. 540,026, filed Jun. 18, 1990) (1.43 mmol) in 15 mL of $CH_2Cl_2$ containing one microdrop of DMF was added 2.0 mL of a 2.0M oxalyl chloride solution in $CH_2Cl_2$. This was stirred for 45 minutes at 23° C. and then concentrated in vacuo to give the corresponding acid chloride. To a slurry of 370 mg (1.0 mmol max.) of crude Part A amine in 45 mL of $CH_2Cl_2$ was added 255 μL of triethylamine (1.8 mmol). To this mixture was then added via cannula a solution of the above acid chloride in 10 mL of $CH_2Cl_2$. This was stirred for 130 minutes at which time 10 mL of saturated aqueous $NaHCO_3$ solution was added. The mixture was stirred vigorously. This caused the formation of a gel; attempted filtration resulted in removal of the organic layer but the aqueous layer had to be removed by decantation. The gel was washed with water (stirred manually). The combined aqueous layers were extracted with 25 mL of $CHCl_3$. The combined organic layers were washed with 15 mL of 0.2N NaOH solution followed by 15 mL of 1N HCl solution. The $CHCl_3$ layer was diluted with $CH_3OH$ to obtain aclear solution and concentrated in vacuo to afford 750 mg of crude title amide. This was chromatographed on 50 g of silica gel using 10% $CH_3OH/CH_2Cl_2$ as eluant to afford 220 mg (30%) of pure title amide.

C.

[1S-(1α,2α,3α,4α)]-2-[[3-[4-[[[8-[[5-(Hexahydro-2-oxo-1H-thieno[3,4-d]imidazol-4-yl)-1-oxopentyl-]amino]octyl]amino]carbonyl]-2-oxazolyl]-7-oxabicyclo[2.2.1]hept-2-yl]methyl]benzenepropanoic acid A solution of 210 mg (0.28 mmol) of Part B amide in 15 mL of distilled THF and 5 mL of CH₃Oh was purged with a stream of argon for 20 minutes. To this solution was added 2 mL of water followed by 23.5 mg of LiOH.H₂O. The reaction mixture was stirred for 5 hours at which time TLC analysis showed some starting material remaining. The reaction was placed in the refrigerator overnight. The following morning the reaction mixture was concentrated in vacuo. The residue was dissolved in 15 mL of water and then 1N HCl solution was added which resulted in the formation of a white precipitate. Twenty-five mL of CHCl₃ was added and then additional 1N HCl was added until the pH of the aqueous layer was 3.5. Layers were separated and then the aqueous layer was extracted with two 25 mL portions of CHCl₃. The combined CHCl₃ layers was diluted with a small amount of isopropyl alcohol, dried over MgSO₄, filtered and concentrated in vacuo to afford 250 mg of crude product. On further removal of solvent, the product solidified. The solid was scraped from the walls of the flask and triturated with hexane to afford 145 mg of title amide as an off-white powder.

TLC: silica gel 10% CH₃OH/CH₂Cl₂+HOAc, R$_f$=0.45; trace impurity, R$_f$=0.6.

Following the procedures of Example 1 and U.S. application Ser. No. 540,026 filed Jun. 18, 1990, the following compounds within the scope of the present invention may be prepared.

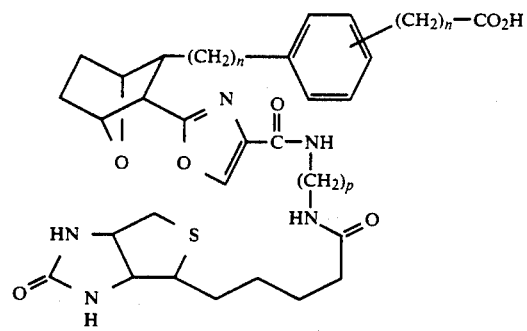

| Ex. No. | m | n | p | (position) |
|---|---|---|---|---|
| 2 | 1 | 2 | 2 | -(2) |
| 3 | 1 | 2 | 3 | -(2) |
| 4 | 1 | 2 | 4 | -(2) |
| 5 | 1 | 2 | 6 | -(2) |
| 6 | 1 | 2 | 10 | -(2) |
| 7 | 1 | 2 | 2 | -(2) |
| 8 | 1 | 2 | 3 | -(2) |
| 9 | 1 | 2 | 14 | -(2) |
| 10 | 1 | 2 | 16 | -(2) |
| 11 | 1 | 2 | 18 | -(2) |
| 12 | 1 | 2 | 4 | -(2) |
| 13 | 1 | 2 | 6 | -(2) |
| 14 | 1 | 2 | 8 | -(2) |
| 15 | 2 | 2 | 2 | -(2) |
| 16 | 3 | 2 | 3 | -(2) |
| 17 | 1 | 3 | 6 | -(2) |
| 18 | 1 | 4 | 9 | -(2) |
| 19 | 1 | 1 | 12 | -(2) |
| 20 | 2 | 3 | 15 | -(2) |
| 21 | 2 | 4 | 18 | -(2) |
| 22 | 3 | 3 | 10 | -(2) |
| 23 | 3 | 4 | 5 | -(2) |

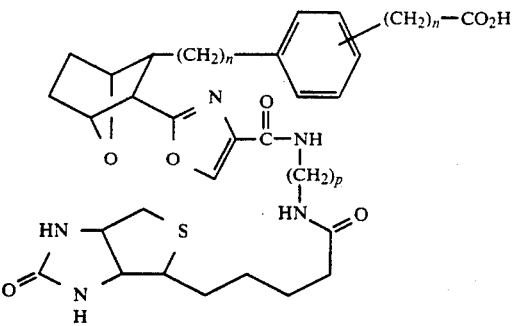

| Ex. No. | m | n | p | (position) |
|---|---|---|---|---|
| 24 | 1 | 2 | 2 | -(3) |
| 25 | 2 | 2 | 3 | -(3) |
| 26 | 1 | 2 | 5 | -(3) |
| 27 | 3 | 2 | 7 | -(3) |
| 28 | 1 | 2 | 9 | -(3) |
| 29 | 2 | 3 | 12 | -(3) |
| 30 | 3 | 4 | 15 | -(3) |
| 31 | 1 | 1 | 18 | -(3) |

What is claimed is:

1. A compound having the formula

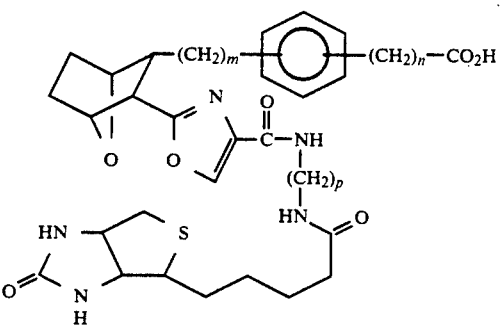

including all stereoisomers thereof, wherein
m is 1, 2 or 3;
n is 1, 2, 3 or 4; and
p is 2 to 18.

2. The compound as defined in claim 1 wherein m is 1 or 2 and n is 2 or 3.

3. The compound as defined in claim 1 wherein m is 1 and n is 2 or 3 and p is 4 to 12.

4. The compound as defined in claim 1 having the formula

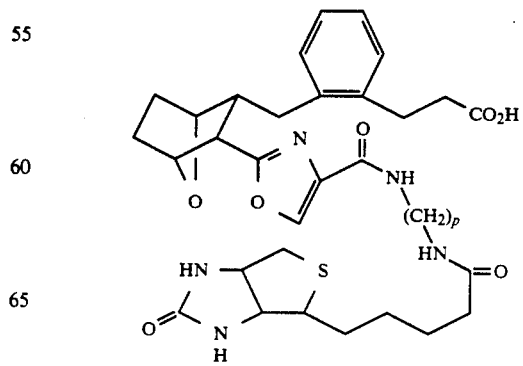

5. The compound as defined in claim 1 which is [1S-(1α,2α,3α,4α)[-2-[[3-[4-[[[8-[[5-(hexahydro-2-oxo-1H-thieno[3,4-d]imidazol-4-yl)-1-oxopentyl]amino]octyl]amino]carbonyl]-2-oxazolyl]-7-oxabicyclo[2.2.1]hept-2-yl]methyl]benzenepropanoic acid.

6. A method of inhibiting platelet aggregation and bronchoconstriction, which comprises administering to the circulatory system of a mammalian host a therapeutically effective amount of a compound as defined in claim 1.

7. A composition for inhibiting platelet aggregation and bronchoconstriction comprising a therapeutically effective amount of a compound as defined in claim 1, and a pharmaceutically acceptable carrier therefor.

8. A method of inhibiting platelet aggregation which comprises administering to a mammalian host a therapeutically effective amount of a compound as defined in claim 1.

9. A method of inhibiting bronchoconstriction associated with asthma, which comprises administering to a mammalian host a therapeutically effective amount of a compound as defined in claim 1.

10. A method for treating toxemia during pregnancy, which comprises admininstering to a mammalian host in need of such treatment a therapeutically effective amount of a compound as defined in claim 1.

11. A method for preventin or reducing venous thrombosis. which comprises administering to a mammalian host in need of such treatment a therapeutically effecitve amount of a compound as defined in claim 1.

12. A method for preventing or reducing platelet loss during extracorporeal circulation which comprises administering to a mammalian host in need of such treatment a therapeutically effective amount of a compound as defined in claim 1.

* * * * *